United States Patent [19]

Hawking

[11] 4,022,881

[45] May 10, 1977

[54] DENTIFRICE

[75] Inventor: Brian Rae Hawking, Twickenham, England

[73] Assignee: Beecham Group Limited, Great Britain

[22] Filed: June 10, 1975

[21] Appl. No.: 585,699

[30] Foreign Application Priority Data

June 18, 1974 United Kingdom ............ 26886/74

[52] U.S. Cl. .................................. 424/52; 424/49
[51] Int. Cl.² ......................................... A61K 7/18
[58] Field of Search ............................ 424/49–58, 424/362; 252/316; 106/197 CM; 260/231 CM

[56] References Cited

UNITED STATES PATENTS

| | | | |
|---|---|---|---|
| 2,618,632 | 11/1952 | Klug | 260/231 |
| 2,839,448 | 6/1958 | Hager et al. | 424/52 |
| 3,014,808 | 12/1961 | Nyberg | 106/197 CM |
| 3,112,247 | 11/1963 | Schweizer | 424/52 |
| 3,151,027 | 9/1964 | Cooley et al. | 424/52 X |
| 3,251,824 | 5/1966 | Battista | 260/231 CM |
| 3,266,996 | 8/1966 | Muhler | 424/52 |
| 3,448,100 | 6/1969 | Callihan et al. | 260/231 CM |
| 3,510,553 | 5/1970 | Mellberg | 424/52 |
| 3,538,230 | 11/1970 | Pader et al. | 424/50 |
| 3,804,946 | 4/1974 | Harrison et al. | 424/54 |
| 3,903,252 | 9/1975 | Stearns et al. | 424/7 |

*Primary Examiner*—Shep K. Rose

[57] ABSTRACT

A dentifrice containing as combined thickening agent 5–30% high viscosity hydroxyethylcellulose and 70–95% sodium carboxymethylcellulose, preferably 10–15% of the former and 85–90% of the latter and being from 0.1–5% by weight of the total dentifrice formulation.

4 Claims, No Drawings

DENTIFRICE

This invention relates to a dentifrice and in particular to a dentifrice with a reduced tendency to lose rigidity and viscosity.

In order to prevent separation of the ingredients of a dentifrice on storage it is necessary to incorporate a binding agent, or thickener. Thickeners used in dentifrices are hydrophilic colloids which disperse in aqueous media. The most commonly used thickeners are cellulose derivatives because they are cheap and their quality can be closely controlled. Sodium carboxymethyl cellulose (NaCMC) is the most widely used dentifrice thickener. Occasionally however, dentifrices incorporating sodium carboxymethyl cellulose are subject to syneresis, i.e. severe loss of rigidity and viscosity. It is believed that this may be caused partly by enzymatic degradation of the NaCMC by cellulytic enzyme (cellulase) which can be produced by moulds and bacteria present in some batches of NaCMC. These microrganisms may originate in the water, or on storage of the NaCMC, in damp conditions which support growth, or from other sources of contamination. Killing the organism responsible does not of course remove the enzyme already produced.

Hydroxyethyl cellulose is a thickener with a better resistance to cellulytic attack than NaCMC, possibly due to its more uniform substitution pattern along the molecule compared with NaCMC, but in dentifrice formulations as the sole thickener, it produces a product with an unacceptably "long" or "stringy" texture.

We have now found that if a minor proportion of high viscosity grade hydroxyethyl cellulose is blended with the sodium carboxymethyl cellulose, the resulting dentifrice is unexpectedly stable to degradation.

Accordingly the present invention provides a dentifrice containing as thickening agent a combination of from 5 to 30% of high viscosity hydroxyethyl cellulose and from 70 to 95% of sodium carboxymethyl cellulose, these percentages being by weight of the hydroxyethyl cellulose/sodium carboxymethyl cellulose combinations.

The term "high viscosity" in relation to hydroxyethyl cellulose means having a viscosity greater than 1500 centipoise in a 1% aqueous solution as measured in a Brookfield Viscometer.

Preferred proportions of hydroxyethyl cellulose are from 10 to 20% more preferably 10 to 15% by weight of the combined thickening agent.

The proportion of combined thickening agent in the dentifrice varies with the form of dentifrice used, but in general may comprise from 0.1 to 5% by weight of the total dentifrice formulations.

The dentifrices of this invention may be in any desired form, for example toothpastes, liquid dentifrices, transparent or transluscent gels, dentifrices in pressure-packs or dental paints, and contain the conventional ingredients of such formulations. Thus a toothpaste for instance will usually comprise an abrasive material, a detergent, humectant, flavouring agent, preservative and colour. Typical toothpaste abrasives include calcium carbonate, calcium phosphates such as dicalcium phosphate, anhydrous or dihydrate, tricalcium phosphate, calcium pyrophosphate, insoluble sodium metaphosphate, magnesium phosphate, magnesium carbonate, various types of alumina and silica, various silicates such as magnesium silicate and aluminium silicate and polymers such as polystyrene, polymethylmethacrylate, polyamines, polycarbonate, polyesters, urea-formaldehyde resins, melamine - formaldehyde resins and phenol-formaldehyde resins.

Commonly-used dental detergents include sodium lauryl sulphate, sodium N-lauroyl sarcosinate and ricinoleate and sulphoricinoleate derivatives.

Suitable humectants include glycerol and sorbitol and also other polyalcohols such as propanediol and/or butanediol.

The dentifrice may also contain the conventional flavouring and sweetening substances such as peppermint or spearmint oil, menthol, chloroform, or oil of clove, wintergreen, eucalyptus, aniseed, rose, lavender; saccharin and sodium cyclamate.

Examples of preservatives which may be incorporated into the dentifrice, include p-hydroxybenzoate esters and hexachlorophene; and known surfactants.

If desired colour may also be imparted to the dentifrice by means of dyestuffs; or bleaches or optical brighteners may be incorporated, such as sodium perborate, magnesium perioxide, hydrogen peroxide-urea compounds.

The hydroxyethylcellulose/sodium carboxymethyl cellulose is equally effective in the presence of fluoride. Thus the toothpaste may also contain a fluorine - containing compound, for example sodium fluoride, stannous fluoride, potassium fluoride, potassium stannous fluoride, sodium hexafluorostannate, stannous chlorofluoride, sodium fluorozirconate and sodium monofluorophosphate.

The invention is illustrated in the following Example:

During the commercial manufacture of toothpaste, a batch of NaCMC had caused severe problems. Toothpaste incorporating this NaCMC as thickening agent simply lost its rigidity and viscosity shortly after manufacture. Experiments with the same grade of NaCMC showed that the problem could be overcome by adding small amounts of high viscosity hydroxyethylcellulose. Specifically it was shown that toothpastes including the following combination thickening agents were stable:

|     | hydroxyethylcellulose (H.E.C.) | NaCMC |
| --- | --- | --- |
| (a) | 5% w/w | 95% w/w |
| (b) | 10% w/w | 90% w/w |
| (c) | 20% w/w | 80% w/w |
| (d) | 25% w/w | 75% w/w |
| (e) | 30% w/w | 70% w/w |

At 30% w/w H.E.C. practical problems arose in filling the paste into tubes, because the paste was somewhat "stringy" in texture. However the manufacturing process could be modified to overcome this problem. It was judged that higher loadings of H.E.C. would produce an unacceptably "stringy" paste.

At 5% w/w H.E.C. protection against degradation was good but it was judged that below this level, protection could not be guaranteed in all cases.

The preferred loading of H.E.C. was judged to be about 10% and an Example of a toothpaste formulation using such a loading is as follows:

|  | % w/w |
| --- | --- |
| Glycerine | 20.0 |
| 70% w/w Sorbitol solution | 5.0 |
| NaCMC | 0.9 |
| H.E.C.* | 0.1 |

-continued

| | % w/w |
|---|---|
| Sodium monofluorophosphate | 0.8 |
| Calcium carbonate | 45.0 |
| Sodium Lauryl Sulphate | 2.0 |
| Flavour | q.s. |
| Water | to 100.0 |

*"Natrosol 250 H" - Hercules Powder Company.

I claim:

1. A toothpaste formulation comprising about 20% w/w glycerine, about 5% w/w of 70% w/w of sorbitol solution, about 20% water, about 45% water-insoluble abrasive and about 0.1–5% w/w of combined thickening agent effective in the presence of a fluorine-containing compound and which makes the toothpaste formulation stable to degradation and resistant to syneresis, said combined thickening agent being about 90% sodium carboxymethylcellulose blended with about 10% hydroxyethylcellulose having a viscosity greater than 1500 cps in a 1% aqueous solution as measured in a Brookfield Viscometer.

2. A toothpaste formulation according to claim 1 in which the combined thickening agent amounts to about 1% w/w.

3. A toothpaste formulation according to claim 1 in which is incorporated a fluorine-containing compound in an amount of about 0.8% w/w.

4. A toothpaste formulation according to claim 3 in which the fluorine-containing compound is sodium monofluorophosphate.

* * * * *